(12) United States Patent
Tepper et al.

(10) Patent No.: US 7,947,648 B2
(45) Date of Patent: May 24, 2011

(54) METHODS FOR TREATING ASTHMA IN HUMAN AND NON HUMAN PRIMATES USING IL-4 MUTANT COMPOSITIONS

(75) Inventors: Jeffrey Tepper, San Carlos, CA (US); Adrian Tomkinson, El Cerrito, CA (US)

(73) Assignee: Aerovance, Inc., Berkeley, CA (US)

( * ) Notice: Subject to any disclaimer, the term of this patent is extended or adjusted under 35 U.S.C. 154(b) by 669 days.

(21) Appl. No.: 11/652,868

(22) Filed: Jan. 11, 2007

(65) Prior Publication Data

US 2007/0212308 A1 Sep. 13, 2007

Related U.S. Application Data

(60) Provisional application No. 60/758,442, filed on Jan. 11, 2006, provisional application No. 60/841,583, filed on Aug. 30, 2006.

(51) Int. Cl.
*A61K 39/00* (2006.01)
*A61K 45/00* (2006.01)
*C12P 21/02* (2006.01)

(52) U.S. Cl. ............... 514/1.7; 424/185.1; 424/85.2; 435/69.52

(58) Field of Classification Search .................. None
See application file for complete search history.

(56) References Cited

U.S. PATENT DOCUMENTS

| 5,017,691 | A | | 5/1991 | Lee et al. |
|---|---|---|---|---|
| 5,783,181 | A | | 7/1998 | Browne et al. ............ 424/85.2 |
| 5,986,059 | A | * | 11/1999 | Shanafelt et al. ........... 530/351 |
| 6,028,176 | A | | 2/2000 | Greve et al. |
| 6,130,318 | A | | 10/2000 | Wild et al. .................. 530/351 |
| 6,313,272 | B1 | | 11/2001 | Greve et al. |
| 6,335,426 | B1 | | 1/2002 | Shanafelt et al. |
| 7,407,957 | B2 | * | 8/2008 | Javaid et al. ................ 514/248 |
| 2003/0004314 | A1 | * | 1/2003 | Shanafelt et al. ............ 530/351 |
| 2005/0059590 | A1 | | 3/2005 | Pan et al. |

FOREIGN PATENT DOCUMENTS

WO WO 97/47744 * 12/1997

OTHER PUBLICATIONS

Kruse, N. et al, "Conversion of human interleukin-4 into a high affinity antagonist by a single amino acid replacement", *The EMBO Journal*, vol. 11, No. 9, pp. 3237-3244, 1992.

Tony, Hans-Peter, et al, "Design of human interleukin-4 antagonists inhibiting interleukin-4-dependent and interleukin-13-dependent responses in T-cells and B-cells with high efficiency", *Eur. J. Biochem*, vol. 225, pp. 659-665, 1994.

* cited by examiner

*Primary Examiner* — Elly-Gerald Stoica
(74) *Attorney, Agent, or Firm* — DLA Piper LLP (US)

(57) ABSTRACT

The present invention relates generally to methods and compounds for treating pulmonary disorders, and more specifically to the inhalation administration and use of hIL-4 mutant proteins to treat asthma.

24 Claims, 8 Drawing Sheets

|         | IC50 (nM) |
|---------|-----------|
| IL-4RA  | 0.5079    |
| Pre Neb | 0.4594    |
| Post Neb| 0.4826    |
| Residual| 0.5741    |

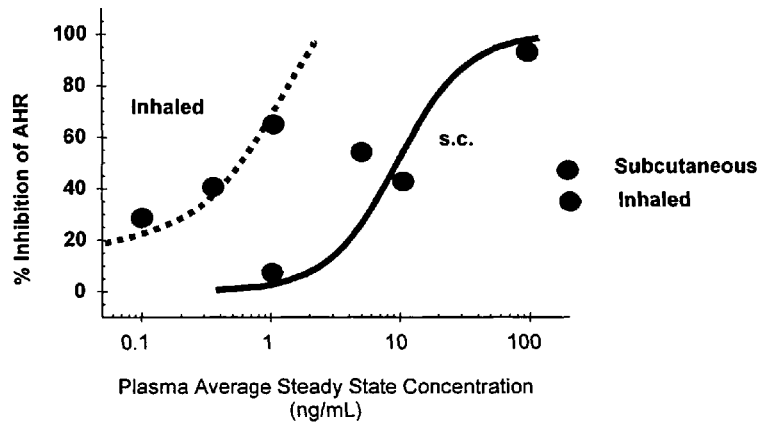

FIGURE 12

HKCDITLQEIIKTLNSLTEQKTLCTELTVTDIFA
ASKNTTEKETFCRAATVLRQFYSHHEKDTRCL
GATAQQFHRHKQLIRFLKRLDRNLWGLAGLN
SCPVKEANQSTLENFLERLKTIMREKYSKCSS cacaagtgcgatatcaccttacaggagatcatcaaaact
ttgaacagcctcacagagcagaagactctgtgcaccgag
ttgaccgtaacagacatctttgctgcctccaagaacacaact
gagaaggaaaccttctgcagggctgcgactgtgctccggca
gttctacagccaccatgagaaggacactcgctgcctgggtgc
gactgcacagcagttccacaggcacaagcagctgatccgat
tcctgaaacggctcgacaggaacctctggggcctggcgggct
tgaattcctgtcctgtgaaggaagccaaccagagtacgttgga
aaacttcttggaaaggctaaagacgatcatgagagagaaata
ttcaaagtgttcgagc

FIGURE 13A

| Met His Lys Cys Asp Ile Thr Leu Gln Glu Ile Ile Lys Thr |
| ATGCACAAATGCGATATCACCCTGCAGGAAATCATCAAAACC |
| Leu Asn Ser Leu Thr Glu Gln Lys Thr Leu Cys Thr Glu Leu |
| CTGAATTCTCTGACCGAACAGAAAACCCTGTGCACCGAACTG |
| Thr Val Thr Asp Ile Phe Ala Ala Ser Lys Asn Thr Thr Glu |
| ACCGTTACCGACATCTTCGCTGCTTCGAAAAACACCACCGAA |
| Lys Glu Thr Phe Cys Arg Ala Ala Thr Val Leu Arg Gln Phe |
| AAAGAAACCTTCTGCCGTGCTGCTACCGTTCTGCGTCAGTTC |
| Tyr Ser His His Glu Lys Asp Thr Arg Cys Leu Gly Ala Thr |
| TACTCTCACCACGAAAAAGACACCCGTTGCCTGGGTGCTACC |
| Ala Gln Gln Phe His Arg His Lys Gln Leu Ile Arg Phe Leu |
| GCTCAGCAGTTCCACCGTCACAAACAGCTGATCCGTTTCCTG |
| Lys Arg Leu Asp Arg Asn Leu Trp Gly Leu Ala Gly Leu Asn |
| AAACGTCTGGACCGTAACCTGTGGGGTCTGGCTGGTCTGAAC |
| Ser Cys Pro Val Lys Glu Ala Asn Gln Ser Thr Leu Glu Asn |
| AGCTGCCCGGTTAAAGAAGCTAACCAGTCTACCCTGGAAAAC |
| Phe Leu Glu Arg Leu Lys Thr Ile Met Asp Glu Lys Asp Ser |
| TTCCTGGAACGTCTGAAAACCATCATGGACGAAAAAGACTCT |
| Lys Cys Ser Ser *** *** |
| AAATGCTCTTCTTAATAA |

FIGURE 13B

SEQUENCE LISTING

```
<160> NUMBER OF SEQ ID NOS: 4

<210> SEQ ID NO 1
<211> LENGTH: 129
<212> TYPE: PRT
<213> ORGANISM: Homo sapiens

<400> SEQUENCE: 1

His Lys Cys Asp Ile Thr Leu Gln Glu Ile Ile Lys Thr Leu Asn Ser
1               5                   10                  15

Leu Thr Glu Gln Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
        35                  40                  45

Ala Thr Val Leu Arg Gln Phe Tyr Ser His His Glu Lys Asp Thr Arg
    50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
        115                 120                 125

Ser

<210> SEQ ID NO 2
<211> LENGTH: 387
<212> TYPE: DNA
<213> ORGANISM: Homo sapiens

<400> SEQUENCE: 2
cacaagtgcg atatcacctt acaggagatc atcaaaactt tgaacagcct cacagagcag      60
aagactctgt gcaccgagtt gaccgtaaca gacatctttg ctgcctccaa gaacacaact     120
gagaaggaaa ccttctgcag ggctgcgact gtgctccggc agttctacag ccaccatgag     180
aaggacactc gctgcctggg tgcgactgca cagcagttcc acaggcacaa gcagctgatc     240
cgattcctga aacggctcga caggaacctc tggggcctgg cgggcttgaa ttcctgtcct     300
gtgaaggaag ccaaccagag tacgttggaa aacttcttgg aaaggctaaa gacgatcatg     360
agagagaaat attcaaagtg ttcgagc                                          387

<210> SEQ ID NO 3
<211> LENGTH: 130
<212> TYPE: PRT
<213> ORGANISM: Artificial sequence
<220> FEATURE:
<223> OTHER INFORMATION: Synthetic construct

<400> SEQUENCE: 3

Met His Lys Cys Asp Ile Thr Leu Gln Glu Ile Ile Lys Thr Leu Asn
1               5                   10                  15
```

```
Ser Leu Thr Glu Gln Lys Thr Leu Cys Thr Glu Leu Thr Val Thr Asp
            20                  25                  30

Ile Phe Ala Ala Ser Lys Asn Thr Thr Glu Lys Glu Thr Phe Cys Arg
            35                  40                  45

Ala Ala Thr Val Leu Arg Gln Phe Tyr Ser His His Glu Lys Asp Thr
 50                  55                  60

Arg Cys Leu Gly Ala Thr Ala Gln Gln Phe His Arg His Lys Gln Leu
 65              70                  75              80

Ile Arg Phe Leu Lys Arg Leu Asp Arg Asn Leu Trp Gly Leu Ala Gly
                85                  90                  95

Leu Asn Ser Cys Pro Val Lys Glu Ala Asn Gln Ser Thr Leu Glu Asn
            100                 105                 110

Phe Leu Glu Arg Leu Lys Thr Ile Met Asp Glu Lys Asp Ser Lys Cys
            115                 120                 125

Ser Ser
    130

<210> SEQ ID NO 4
<211> LENGTH: 396
<212> TYPE: DNA
<213> ORGANISM: Artificial sequence
<220> FEATURE:
<223> OTHER INFORMATION: Synthetic construct

<400> SEQUENCE: 4
atgcacaaat gcgatatcac cctgcaggaa atcatcaaaa ccctgaattc tctgaccgaa      60
cagaaaaccc tgtgcaccga actgaccgtt accgacatct cgctgcttc gaaaaacacc     120 accgaaaaag aaaccttctg ccgtgctgct accgttctgc gtcagttcta ctctcaccac     180 gaaaagaca cccgttgcct gggtgctacc gctcagcagt tccaccgtca caaacagctg     240
atccgtttcc tgaaacgtct ggaccgtaac ctgtggggtc tggctggtct gaacagctgc     300
ccggttaaag aagctaacca gtctacccctg gaaaacttcc tggaacgtct gaaaaccatc     360
atggacgaaa aagactctaa atgctcttct taataa                               396
```

METHODS FOR TREATING ASTHMA IN HUMAN AND NON HUMAN PRIMATES USING IL-4 MUTANT COMPOSITIONS

CROSS REFERENCE TO RELATED APPLICATION(S)

This application claims the benefit of priority under 35 U.S.C. §119(e) of U.S. Ser. No. 60/758,442, filed Jan. 11, 2006, and to U.S. Ser. No. 60/841,583, filed Aug. 30, 2006, the entire contents of which are incorporated herein by reference.

BACKGROUND OF THE INVENTION

1. Field of the Invention

The present invention relates generally to methods and compounds for treating pulmonary disorders, and more specifically to the use of hIL-4 mutant proteins to treat asthma.

2. Background Information

Interleukin-4 (IL-4) and Interleukin-13 (IL-13) are pleiotropic cytokines with a broad spectrum of biological effects on several target cells important in the pathogenesis of atopy and asthma. IL-4 is increasingly appreciated as the pivotal cytokine initiating the "Th2-type" inflammatory response forming the underling milieu necessary for the development of atopy and asthma. IL-4 effects include activation, proliferation and differentiation of T and B cells. During proliferation of B-lymphocytes, IL-4 acts as a differentiation factor by regulating class switching from IgG to IgE thus, encouraging the development of allergic reactions. IL-13 is now appreciated as the more probable downstream effector cytokine. IL-13 dominant effects include induction of airways hyperresponsiveness (AHR) and goblet cell hyperplasia, both cardinal features of asthma. However, there is considerable redundancy in the effects of these two cytokines.

The redundancy in effects associated with the binding and signaling of these two cytokines can be explained by their sharing of common receptors. The IL-4 receptor alpha chain (IL-4Rα) has two binding partners with which it can associate and signal. IL-4Rα polypeptide associates with the cytokine common receptor gamma chain (γc) to form the type 1 IL-4R receptor heterodimer. IL-4Rα polypeptide can also form a heterodimer with the IL-13 receptor alpha 1 chain to create the type 2 IL-4R (aka IL-13R). IL-4 activates both the type 1 and type 2 receptors whereas IL-13 only activates the type 2 receptor heterodimer. Both receptors, when activated, signal through the transcription factor signal transducer and activator of transcription 6 (STAT6). Although IL-4 may uniquely initiate the T-helper 2 (Th2) pathway, since only type 1 receptors are localized to T lymphocytes, IL-13 may be both more abundant and more potent. Thus inhibition of both cytokines is important in disease states regulated and controlled by the production of these two cytokines.

Recently, certain antagonistic and partially antagonistic properties have been observed in human IL-4 (hIL-4) mutant proteins in which the amino acid(s) occurring naturally in the wild type at one or more of positions 120, 121, 122, 123, 124, 125, 126, 127 or 128 have been replaced with one or more natural amino acids. Thus, these hIL-4 muteins have been described as valuable therapeutic agents for use as medicaments in treating overshooting or falsely regulated immune reactions and autoimmune diseases.

SUMMARY OF THE INVENTION

The present invention is based, in part, on the finding that mutant IL-4 proteins are useful in treating subjects having asthma. The invention is based in part on the finding that a mutant IL-4 protein having substitutions of R121D and Y124D can be administered in a pharmaceutical composition to antagonize the binding of wild-type hIL-4 and wild-type hIL-13 to receptors.

Accordingly, in one embodiment, the present invention provides methods of treating asthma by administration of mutant IL-4 proteins. In one embodiment, the method for treating asthma includes administering to a subject in need thereof, a pharmaceutical composition containing a therapeutically effective amount of an IL-4 mutant protein having the amino acid sequence of wild-type hIL-4 with substitutions R121D and Y124D numbered in accordance with the wild-type hIL-4. In one aspect, the composition is aerosolized prior to administration, and thus may be administered via inhalation once or twice per day. Typical amounts of the mutant IL-4 protein per dose are greater than or equal to 0.5 mg nominal dose in the nebulizer. The subject may be a mammal, such as a human.

A pharmaceutical composition containing the mutant IL-4 protein of the invention typically contains a pharmaceutically acceptable carrier, such as saline. In other embodiments, the mutant IL-4 protein is conjugated to a non-protein polymer. Non-protein polymers useful in the invention include, but are not limited to, hydrophilic polymers, such as polyvinylpyrrolidone, and hydrophobic polymers, such as polyethylene glycol.

The present invention further relates to methods of monitoring a therapeutic regimen for treating a subject having asthma. In one embodiment, the method of monitoring a therapeutic regimen for treating a subject having asthma includes determining a change in lung function, including the immediate and late asthmatic response, airway hyperreactivity and markers of inflammation found in the bronchoalveolar lavage (BAL), serum or exhaled breath. The monitoring is accomplished by detecting a change in the influx of inflammatory cells and mediators in the subject's airway or blood. In another embodiment, the method of monitoring a therapeutic regimen for treating a subject having asthma includes determining a change in BAL eosinophil concentration during therapy. A decrease in BAL eosinophil concentration during therapy is indicative of positive therapeutic effect. In a further embodiment, the method of monitoring includes determining the expired nitric oxide concentration during therapy in comparison to expired nitric oxide prior to therapy. A decrease in expired nitric oxide concentration during or following therapy is indicative of positive therapeutic effect.

BRIEF DESCRIPTION OF THE DRAWINGS

FIG. 12 is a graphical representation showing that IL-4RA was more efficacious at lower plasma concentrations when delivered by inhalation, as compared to subcutaneous delivery in non-human primates.

FIGS. 13A and 13B show the nucleic acid and amino acid sequences for wt IL-4 (SEQ ID NOs: 1 and 2) and a mutant IL-4 (SEQ ID NOs: 3 and 4), respectively.

DETAILED DESCRIPTION OF THE INVENTION

Figure 1:
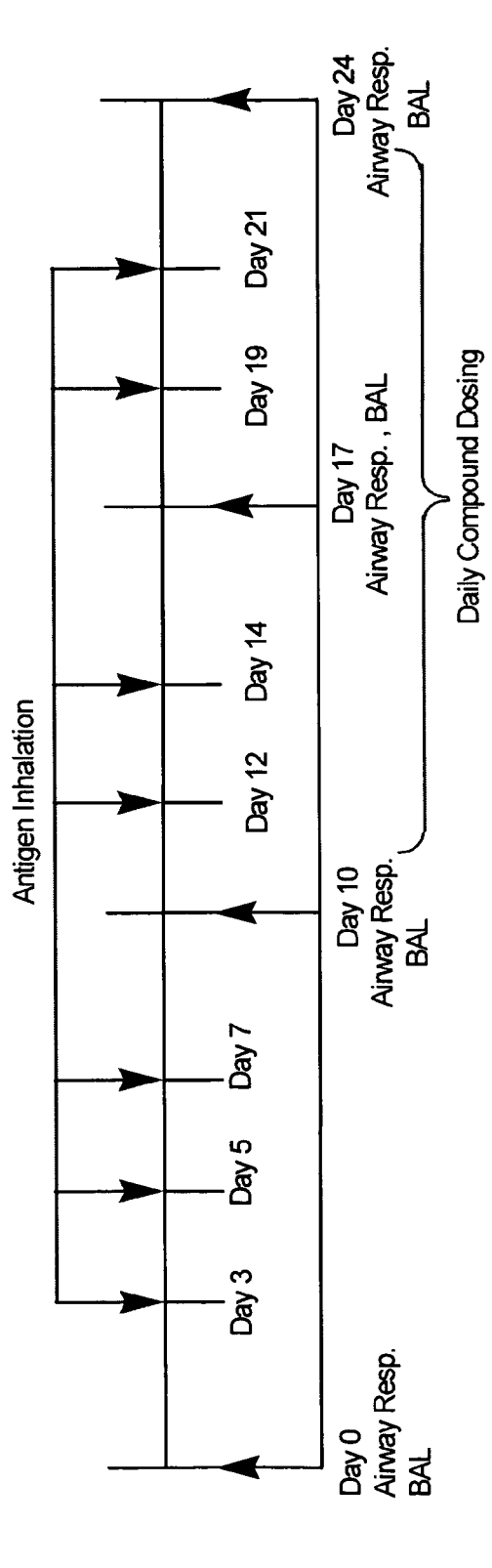
FIG. 1 is a graphical representation showing the primate asthma model therapeutic intervention protocol.

The present invention is based on the finding that hIL-4 muteins are useful for treating asthma. Thus, the present invention discloses methods and compositions of treating asthma with therapeutically effective amounts of mutant IL-4 proteins and pharmaceutical compositions containing the muteins.

The present invention is not limited to the particular methodology, protocols, cell lines, vectors, reagents, etc., described herein, as these may vary. It is also to be understood that the terminology used herein is used for the purpose of describing particular embodiments only, and is not intended to limit the scope of the present invention. As used herein and in the appended claims, the singular forms "a," "an," and "the" include plural reference unless the context clearly dictates otherwise.

The term "asthma" is used herein to generally describe a chronic respiratory disease, often arising from allergies, that is characterized by sudden recurring attacks of labored breathing, chest constriction, and coughing. In a typical asthmatic reaction, IgE antibodies predominantly attach to mast cells that lie in the lung interstitium in close association with the bronchioles and small bronchi. An antigen entering the airway will thus react with the mast cell-antibody complex, causing release of several substances, including, but not limited to interleukin cytokines, chemokines and arachodonic acid derived mediators, resulting in bronchoconstriction, airway hyperreactivity, excessive mucus secretion and airway inflammation. Thus, in certain embodiments of the invention, the treatment of asthma may include the treatment of airway hyperreactivity and/or the treatment of lung inflammation.

The term "antigen" as used herein refers to any substance that when introduced into the body stimulates the production of an antibody. Antigens include insect, animal and plant proteins, toxins, bacteria, foreign blood cells, and the cells of transplanted organs. "Allergens" refer to any substances that cause an allergic immune reaction in a subject. Typically, allergens are from foods, plants, insects or animals that inflame the airway and cause mucus production and bronchoconstriction.

The term "subject" as used herein refers to any individual or patient to which the subject methods are performed. Generally the subject is human, although as will be appreciated by those in the art, the subject may be an animal. Thus, other animals, including mammals such as rodents (including mice, rats, hamsters and guinea pigs), cats, dogs, rabbits, farm animals including cows, horses, goats, sheep, pigs, etc., and non human primates (including monkeys, chimpanzees, orangutans and gorillas) are included within the definition of subject.

As used herein, the terms "mutant human IL-4 protein," "modified human IL-4 receptor antagonist," "mhIL-4," "IL-4 mutein," "IL-4 antagonist," and equivalents thereof are used interchangeably and are within the scope of the invention. These polypeptides and functional fragments thereof refer to polypeptides wherein specific amino acid substitutions to the mature human IL-4 protein have been made. These polypeptides include the mhIL-4 compositions of the present invention, which are administered to a subject in need of treatment for asthma. In particular, the mhIL-4 of the present invention, include at least the R121D/Y124D pair of substitutions ("IL-4RA") (FIG. 13B).

As used herein, a "functional fragment" is a polypeptide which has IL-4 antagonistic activity, including smaller peptides. These and other aspects of mhIL-4 of modification of hIL-4 are described in U.S. Pat. Nos. 6,335,426; 6,313,272; and 6,028,176, the entire contents of which are incorporated herein by reference.

As used herein, "wild type IL-4" or "wtIL-4" and equivalents thereof are used interchangeably and mean human Interleukin-4, native or recombinant, having the 129 normally occurring amino acid sequence of native human IL-4, as disclosed in U.S. Pat. No. 5,017,691, incorporated herein by reference. Further, the modified human IL-4 receptor antagonists described herein may have various insertions and/or deletions and/or couplings to a non-protein polymer, and are numbered in accordance with the wtIL-4, which means that the particular amino acid chosen is that same amino acid that normally occurs in the wtIL-4. Accordingly, one skilled in the art will appreciate that the normally occurring amino acids at positions, for example, 121 (arginine), 124 (tyrosine), and/or 125 (serine), may be shifted in the mutein. Thus, an insertion of a cysteine residue at amino acid positions, for example, 38, 102 and/or 104 may be shifted on the mutein. However, the location of the shifted Ser (S), Arg (R), Tyr (Y) or inserted Cys (C) can be determined by inspection and correlation of the flanking amino acids with those flanking Ser, Arg, Tyr or Cys in wtIL-4.

Further, the DNA sequence encoding human IL-4 may or may not include DNA sequences that encode a signal sequence. Such signal sequence, if present, should be one recognized by the cell chosen for expression of the IL-4 mutein. It may be prokaryotic, eukaryotic or a combination of the two. It may also be the signal sequence of native IL-4. The inclusion of a signal sequence depends on whether it is desired to secrete the IL-4 mutein from the recombinant cells in which it is made. If the chosen cells are prokaryotic, it generally is preferred that the DNA sequence not encode a signal sequence but include an N-terminal methionine to direct expression. If the chosen cells are eukaryotic, it generally is preferred that a signal sequence be encoded and most preferably that the wild-type IL-4 signal sequence be used, as disclosed in U.S. Pat. No. 6,028,176, incorporated herein by reference. In one illustrative example, a mutant human IL-4 protein of the invention includes the amino acid sequence of wild-type hIL-4 with modifications, wherein a first modification is replacement of one or more of the amino acids occurring in the wild-type hIL-4 protein at positions 121, 124 or 125 with another natural amino acid, and further optionally comprising an N-terminal methionine. In another example, the mutant protein further includes a second modification selected from the group consisting of:

i) the modification of the C-terminus therein;
ii) the deletion of potential glycosylation sites therein;
iii) the coupling of the protein to a non-protein polymer, and any combination thereof.

In yet another example, the mutant protein includes a first modification of the protein that includes substitutions R121D and Y124D, numbered in accordance with the wild-type hIL-4.

As used herein, "mutein" refers to any protein arising as a result of a natural mutation or a site-directed amino acid substitution to any protein created by a person skilled in the art. "Glycosylation" refers to the addition of glycosyl groups to a protein to form a glycoprotein. As such, the term includes both naturally occurring glycosylation and synthetic glycosylation, such as the linking of a carbohydrate skeleton to the side chain of an asparagine residue ("N-glycosylation") or the coupling of a sugar, preferably N-acetylgalactosamine, galactose or xylose to serine, threonine, 4-hydroxyproline or 5-hydroxylysine (O-glycosylation).

Accordingly, the present invention relates to compositions comprising one or more hIL-4 muteins that are antagonists of the human interleukin-4 and/or the human interleukin-13 by interfering with the binding of these two interleukins to the type 1 and type 2 IL-4R. Such compositions are useful for treating subjects having asthma or asthmatic-related symptoms. The hIL-4 muteins may further include modifications in addition to the replacement(s) at positions 121, 124 or 125. These modifications are carried out in order to increase the stability of the hIL-4 muteins, in order to extend the biological half life or in order to facilitate the preparation and purification process. As used herein, the term "agonist" refers to an agent or analog that binds productively to a receptor and mimics its biological activity. The term "antagonist" refers to an agent that binds to receptors but does not provoke the normal biological response and blocks or partially blocks the activity of the agonist.

Antagonists to IL-4 have been reported in the literature. Mutants of IL-4 that function as antagonists include the IL-4 antagonist mutein IL-4/Y124D (Kruse, N., Tony, H. P., Sebald, W., Conversion of human interleukin-4 into a high affinity antagonist by a single amino acid replacement, *Embo J.* 11:3237-44, 1992) and a double mutein IL-4[R121D/Y124D] (Tony, H., et al., Design of Human Interleukin-4 Antagonists in Inhibiting Interleukin-4-dependent and Interleukin-13-dependent responses in T-cells and B-cells with high efficiency, *Eur. J. Biochem.* 225:659-664 (1994)). The single mutein is a substitution of tyrosine by aspartic acid at position 124 in the D-helix. The double mutein is a substitution of arginine by aspartic acid at position 121, and of tyrosine by aspartic acid at position 124 in the D-helix, as disclosed in U.S. Pat. Nos. 6,313,272 and 6,028,176, incorporated herein by reference. Variations in this section of the D helix positively correlate with changes in interactions at the second binding region of the IL-4RA chain.

In one embodiment, the mutein is coupled to a non-protein polymer at various amino acid residues, in particular, at positions 28, 36, 37, 38, 102, 104, 105 or 106. The amino acid positions are numbered according to the wild type IL-4 (i.e. human interleukin-4) amino acid sequence (see U.S. Pat. No. 5,017,691 which is incorporated herein by reference). Non-protein polymers include, for example polyethylene glycol, polypropylene glycol or polyoxyalkylenes, as described in U.S. Pat. Nos. 4,640,835; 4,496,689; 4,301,144; 4,670,417; 4,791,192 or 4,179,337, the entire contents of which are incorporated herein by reference.

Accordingly, one of skill in the art will be able to determine suitable variants of the polypeptide and functional fragment thereof as set forth herein using well-known techniques. As such, the skilled artisan may identify (1) suitable areas of the polypeptide that may be changed without destroying activity by targeting regions not believed to be important for activity (see Kreitman et al. (1994) Biochemistry 33:11637-11644, incorporated herein by reference); (2) residues and portions of the polypeptides that are conserved among similar polypeptides; and (3) areas that may be important for biological activity or for structure that can still be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, the skilled artisan can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of a polypeptide with respect to its three dimensional structure. In certain embodiments, one skilled in the art may choose to not make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays known in the art. Such variants could be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult, 1996, *Curr. Op. in Biotech.* 7:422-427; Chou et al., 1974, *Biochemistry* 13:222-245; Chou et al., 1974, *Biochemistry* 113:211-222; Chou et al., 1978, *Adv. Enzymol Relat. Areas Mol. Biol.* 47:45-148; Chou et al., 1979, *Ann. Rev. Biochem.* 47:251-276; and Chou et al., 1979, *Biophys. J.* 26:367-384. Moreover, computer programs are currently available to assist with predicting secondary structure. One method of predicting secondary structure is based upon homology modeling. For example, two polypeptides or proteins that have a sequence identity of greater than about 30%, or similarity greater than 40% often have similar structural topologies. The recent growth of the protein structural database has provided enhanced predictability of secondary structure, including the potential number of folds within a polypeptide's or protein's structure. See Holm et al., 1999, *Nucl. Acid. Res.* 27:244-247.

It has been suggested (Brenner et al., 1997, *Curr. Op. Struct. Biol.* 7:369-376) that there are a limited number of folds in a given polypeptide or protein and that once a critical number of 5 structures have been resolved, structural prediction will become dramatically more accurate.

In one embodiment, the invention provides methods useful as part of a treatment regimen for asthma. The methods include administration of a pharmaceutical composition comprising a therapeutically effective amount of a mutein of the invention, in which amino acid 121 (arginine) and amino acid 124 (tyrosine) are replaced with aspartic acid (IL-4RA; see FIG. 13B). As provided herein, further modification of the mutein may include one or more of the following: the N terminus and/or C terminus of the molecule being modified, one or more polyethylene glycol molecules being covalently bonded to the molecule, and glycosylation sites which are present in the molecule being partially or completely deleted.

The terms "administration" or "administering" are defined to include an act of providing a compound or pharmaceutical composition of the invention to a subject in need of treatment. The term "therapeutically effective amount" or "effective amount" means the amount of a compound or pharmaceutical composition that will elicit the biological or medical response of a tissue, system, animal or human that is being sought by the researcher, veterinarian, medical doctor or other clinician.

In one embodiment, the pharmaceutical composition includes a mutein having an N-terminus modification that is an insertion of an amino acid, at amino acid position +2. In another embodiment, the mutein has a C-terminus modification that is a deletion of at least one, at least two, at least three, at least four and at least five amino acids. However, deletions of greater than five amino acids from the C-terminus may affect the activity of the mutein. Activity of the mutein from any of the modifications mentioned above and herein can be determined by using any of the methods described previously in related applications and/or patents, and methods described herein (e.g., the Bimolecular Interaction Analysis (BIA) and proliferative assays as described in U.S. application Ser. No. 10/820,559, the entire contents of which is incorporated herein by reference.

Muteins useful in the methods of the invention may further include glycosylation variants wherein the number and/or type of glycosylation site has been altered compared to the amino acid sequences of the parent polypeptide. In certain embodiments, protein variants comprise a greater or a lesser number of N-linked glycosylation sites than the native protein. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created Additional variants include cysteine variants wherein one or more cysteine residues are added to, deleted from or substituted for another amino acid (e.g., serine) compared to the parent amino acid sequence. Cysteine variants may be useful when proteins must be refolded into a biologically active conformation such as after the isolation of insoluble inclusion bodies. In one embodiment, cysteine variants will have fewer cysteine residues than the native protein, and an even number of cysteines to minimize interactions resulting from unpaired cysteines. In another embodiment, the cysteine variants will permit site-specific coupling of at least one non-protein polymer, such as a polyethylene glycol (PEG) molecule, to the mutein.

Further variants include, but are not limited to, mutations such as substitutions, additions, deletions, or any combination thereof, and are typically produced by site-directed mutagenesis using one or more mutagenic oligonucleotide(s) according to methods described herein, as well as according to methods known in the art (see, for example, Sambrook et al., MOLECULAR CLONING: A LABORATORY MANUAL, 3rd Ed., 2001, Cold Spring Harbor, N.Y. and Berger and Kimmel, METHODS IN ENZYMOLOGY, Volume 152, Guide to Molecular Cloning Techniques, 1987, Academic Press, Inc., San Diego, Calif., which are incorporated herein by reference).

Amino acid substitutions of the invention include those substitutions that: (1) reduce susceptibility to proteolysis, (2) reduce susceptibility to oxidation, (3) alter binding affinity for forming protein complexes, (4) alter binding affinities, and/or (5) confer or modify other physicochemical or functional properties on such polypeptides. According to certain embodiments, single or multiple amino acid substitutions (and in some cases, conservative amino acid substitutions) may be made in the naturally occurring sequence (e.g., in the portion of the polypeptide outside the domain(s) forming intermolecular contacts).

Thus, a conservative amino acid substitution typically does not substantially change the structural characteristics of the nucleotide sequence (e.g., a replacement amino acid should not tend to break a helix that occurs in the nucleotide sequence, or disrupt other types of secondary structure that characterizes the nucleotide sequence). Examples of art-recognized polypeptide secondary and tertiary structures are described in PROTEINS, STRUCTURES AND MOLECULAR PRINCIPLES, (Creighton, Ed.), 1984, W.H. Freeman and Company, New York; INTRODUCTION TO PROTEIN STRUCTURE (C. Branden and J. Tooze, eds.), 1991, Garland Publishing, New York, N.Y.; and Thornton et al., 1991, *Nature* 354:105, each of which are incorporated herein by reference.

Peptide analogs are commonly used in the pharmaceutical industry as non-peptide drugs with properties analogous to those of the template peptide. These types of non-peptide compound are termed "peptide mimetics" or "peptidomimetics". See Fauchere, 1986, *Adv. Drug Res.* 15:29; Veber & Freidinger, 1985, *TINS* p. 392; and Evans et al., 1987, *J. Med. Chem.* 30:1229, which are incorporated herein by reference. Such compounds are often developed with the aid of computerized molecular modeling. Peptide mimetics that are structurally similar to therapeutically useful peptides may be used to produce a similar therapeutic or prophylactic effect. Generally, peptidomimetics are structurally similar to a paradigm polypeptide (i.e., a polypeptide that has a biochemical property or pharmacological activity), such as a human antibody, but have one or more peptide linkages optionally replaced by a linkage selected from: —CH2-NH—, —CH2-S—, —CH2-CH2-, —CH=CH-(cis and trans), —COCH2-, —CH(OH) CH2-, and —CH2SO—, by methods well known in the art. Systematic substitution of one or more amino acids of a consensus sequence with a D-amino acid of the same type (e.g., D-lysine in place of L-lysine) may be used in certain embodiments to generate more stable peptides. In addition, constrained peptides comprising a consensus sequence or a substantially identical consensus sequence variation may be generated by methods known in the art (Rizo & Gierasch, 1992, *Ann. Rev. Biochem.* 61:387, incorporated herein by reference); for example, by adding internal cysteine residues capable of forming intramolecular disulfide bridges which cyclize the peptide.

In another embodiment, the pharmaceutical composition includes a mutein (e.g., IL-4RA) having additional amino acid substitutions, including those substitutions that enable the site-specific coupling of at least one non-protein polymer, such as polypropylene glycol, polyoxyalkylene, or polyethylene glycol (PEG) molecule to the mutein. Site-specific coupling of PEG, for example, allows the generation of a modified mutein which possesses the benefits of a polyethylene-glycosylated (PEGylated) molecule, namely increased plasma half life (e.g., at least 2 to 10-fold greater, or 10 to 100-fold greater than that of unmodified IL-4RA) while maintaining greater potency over non-specific PEGylation strategies such as N-terminal and lysine side-chain PEGylation. Methods providing for efficient PEGylation are described in U.S. application Ser. No. 10/820,559, which is incorporated herein by reference. The IL-4 mutein must be purified properly to allow efficient PEGylation. Purification is described in U.S. application Ser. No. 10/820,559 (see Example 2).

The Ki of modified IL-4 mutein receptor antagonists to the IL-4 receptor can be assayed using any method known in the art, including technologies such as real-time Bimolecular Interaction Analysis (BIA) as described in U.S. application Ser. No. 10/820,559 (see Example 4). The capacity of modified IL-4 mutein receptor antagonists to inhibit the proliferative response of immune cells can be assessed using proliferative assays as described in U.S. application Ser. No. 10/820,559.

A number of modified IL-4 mutein receptor antagonists with the characteristics described above have been identified in U.S. application Ser. No. 10/820,559, by screening candidates with the above assays. In one embodiment, a non-protein polymer (e.g., polyethylene glycol) is coupled to at least amino acid residue positions 38, 102 and/or 104.

In another embodiment, the invention provides methods of selecting the specific sites of amino acid substitution of hIL-4 that enables proper folding of the polypeptide following expression. Modified IL-4 mutein receptor antagonists bind to IL-4 and IL-13 receptors with an affinity loss not greater than 100-fold relative to that of unmodified IL-4RA. Modified IL-4 mutein receptor antagonists inhibit IL-4 and IL-13 mediated activity with a loss of potency not greater than 10-fold relative to that of unmodified IL-4RA. In addition, modified IL-4 mutein receptor antagonists possess a plasma half-life which is at least 2 to 10-fold greater than that of unmodified IL-4RA.

The above polypeptide variants are illustrative of the types of modified human IL-4 polypeptides to be used in the methods claimed herein, but are not exhaustive of the types of variations of the claimed invention which may be embodied by the invention. Derivatives of the above polypeptide which fit the criteria of the claims should also be considered. All of the polypeptides and functional fragments thereof can be screened for efficacy following the methods taught herein and in the examples.

hIL-4 can be produced as a recombinant protein (rhIL-4) by genetic manipulation, for example in *E. coli*. Host cells suitable for the recombinant production of rhIL-4 are known to those skilled in the art including prokaryotic cells such as strains of *E. coli, Bacillus* or *Pseudomonas* (Kung, H.-F., M. Boublik, V. Manne, S. Yamazaki and E. Garcia, *Curr. Topics in Cell. Reg.* 26: 531-542, 1995) or unicellular eukaryotic cells as yeast *Saccharomyces cerevisiae* (Bemis, L. T., F. J. Geske and R. Strange, *Methods Cell Biol.,* 46: 139-151, 1995). Host cells for recombinant production may also be derived from multicellular eukaryotes comprising invertebrates as insects (*Spodoptera frugiperda* Sf9 cells) (Altmann F., E. Staudacher, I B Wilson, and L Marz, Glycoconj J., 16: 109-123, 1999) and vertebrate cells, including numerous mammalian cell lines comprising mouse fibroblasts, Chinese hamster ovary cells (CHO/-DHFR) (Urlaub and Chasin, *Proc Nat Acad Sci* 77:4216, 1980), baby hamster kidney (9BHK, ATCC CCL 10); monkey kidney CV1 line transformed by SV40 (COS-7, ATCC CRL 1651) and human embryonic kidney cell line 293 (Tartaglia et al., *Proc Nat Acad Sci* 88: 9292-9296, 1991 and Pennica et al., *J. Biol. Chem.* 267: 21172-21178, 1992).

Any suitable host may be used to produce the IL-4 muteins of the current invention, including bacteria, fungi (including yeasts), plant, insect, mammal, or other appropriate animal cells or cell lines, as well as transgenic animals or plants. As such, these hosts may include well known eukaryotic and prokaryotic hosts, such as strains of *E. coli, Pseudomonas, Bacillus, Streptomyces*, fungi, yeast, insect cells such as *Spodoptera frugiperda* (SF9), animal cells such as Chinese hamster ovary (CHO) and mouse cells such as NS/O, African green monkey cells such as COS 1, COS 7, BSC 1, BSC 40, and BNT 10, and human cells, as well as plant cells in tissue culture. Although bacteria and yeast have been the standard recombinant host cells for many recombinant polypeptides, including rhIL-4, recently transformed cells from higher plants are able to express human recombinant proteins as antibodies (Hiatt, A. T. and J. K. Ma, *Int. Rev. Immunol.,* 10: 139-152, 1993) and hemoglobin (Theisen, M. in Chemicals Via Higher Plant Bioengineering, F. Shahidi et al., eds, Plenum Publishers, NY, p. 211-220, 1999). Plant biotechnology offers many advantages for efficient production of heterologous polypeptides, and this approach may be useful for production of the modified human IL-4 receptor antagonists described herein, including mhIL-4 and its derivatives (see also Plant Technology: New Products and Applications, John Hammond, et al., eds., Springer, N.Y., 1999).

The formation of the stable complex of IL-4 or IL-13 to the type 1 or type 2 IL-4 receptor allows receptor signaling and resultant downstream events are believed to cause asthmatic symptoms in subjects. Thus, in one embodiment, the invention provides a method of administering a therapeutically effective amount of modified human IL-4 receptor antagonist, including IL-4RA, to a subject to ameliorate symptoms associated with asthma. Data suggests that IL-4RA binds to the IL-4 receptor a chain with similar on and off rates as wtIL-4, which inhibits assembly of either γc (type 1) or IL-13Rα1 (type 2) into receptor complexes that signal downstream events (see Table 1). Thus, IL-4RA blocks recruitment of either IL-13Rα1 or γc to form a stable heterodimeric complex with the IL-4 receptor a chain (A. L. Andrews et al., ATS 2004).

TABLE 1

Biacore binding of IL-4RA to the immobilized IL-4 receptor α chain.

| | $K_{on}$ $10^6$/Ms | $K_{off}$ $10^{-3}$/s | Affinity (nM) |
|---|---|---|---|
| IL-4RA | 16 | 1.7 | 0.14 ± 0.05 (n = 7) |

Although the invention describes various dosages, it will be understood by one skilled in the art that the specific dose level and frequency of dosage for any particular subject in need of treatment may be varied and will depend upon a variety of factors. These factors include the activity of the specific polypeptide or functional fragment thereof, the metabolic stability and length of action of that compound, the age, body weight, general health, sex, diet, mode and time of administration, rate of excretion, drug combination, the severity of the particular condition, and the host undergoing therapy. Generally, however, dosage will approximate that which is typical for known methods of administration of the specific compound. Thus, a typical dosage of IL-4RA will be about 0.1 to 1 mg/kg. In one illustrative example, an approximate dosage for administration of IL-4RA by subcutaneous injection includes, but is not limited to, about 25 mg. In another illustrative example, for administration of IL-4RA, an approximate dosage by aerosol inhalation would be about 0.3 mg to 60 mg. Approximate dosages include, but are not limited to about 0.3 mg, about 0.5 mg, about 1.0 mg, about 3.0 mg, about 20 mg, about 30 mg or about 60 mg, to a subject, with dosages administered one or more times per day or week. Treatment by administration of IL-4RA may span days, weeks, years, or continue indefinitely, as symptoms persist. Hence, an appropriate dose and treatment regimen can be determined by one of ordinary skill in the art using routine procedures such as those provided herein.

The compositions and formulations of the invention can be administered systemically or locally, i.e., topically, inter alia as an aerosol, such as a nebulized inhalation spray or a dry powder aerosol. As used herein, "systemic administration" or "administered systemically" refers to compositions or formulations that are introduced into the blood stream of a subject, and travel throughout the body of the subject to reach the part of the subject's body in need of treatment at an effective dose before being degraded by metabolism and excreted. Systemic administration of compositions or formulations can be achieved, for example, by oral application (e.g., syrups, tablets, capsules and the like), needle injection, transdermal delivery (e.g., a composition incorporated into a skin patch), and subdermal delivery (e.g., a formulation in a metabolizable matrix placed beneath the skin to be released. As used herein, "local administration" or "administered locally" refers to compositions or formulations that are introduced directly to part of the subject's body in need of treatment. Compositions or formulations can be delivered locally, for example, by injection (e.g., injection of anesthetic into a patient's gums) or topically (e.g., creams, ointments, and sprays). It should be understood that local administration can result in systemic levels of the composition or formulation following administration (e.g., an inhaled composition may result in systemic levels of the composition).

As used herein, the term "aerosol" refers to any gaseous suspension of fine solid or liquid particles. As such, the term "aerosolized" refers to being in the form of microscopic solid or liquid particles dispersed or suspended in air or gas. A typical microscopic solid will have a mass median aerodynamic diameter $\leq 20$ μm. As used herein, the term "nebulize" refers to the act of converting (a liquid) to a fine spray or atomizing. Accordingly, the term "dry powder aerosol" refers to any microscopic solid suspended in gas, typically air. It is also possible for the compositions of the invention to be formulated as a slow-release preparation. A short-term therapy or a continuous therapy is possible in the case of all the therapy forms.

Therapeutic formulations of the IL-4 antagonist are prepared for administration and/or storage by mixing the IL-4 antagonist, after achieving the desired degree of purity, with pharmaceutically and/or physiologically acceptable carriers, auxiliary substances or stabilizers (Remington's Pharmaceutical Sciences, loc. cit.) in the form of a lyophilisate or aqueous solutions. The term "pharmaceutically acceptable" or "physiologically acceptable," when used in reference to a carrier, is meant that the carrier, diluent or excipient must be compatible with the other ingredients of the formulation and not deleterious to the recipient thereof.

In general, the pharmaceutical compositions are prepared by uniformly and intimately bringing the active ingredient into association with a liquid carrier or a finely divided solid carrier or both, and then, if necessary, shaping the product into the desired formulation. Acceptable carriers, auxiliary substances or stabilizers are not toxic for the recipient at the dosages and concentrations employed; they include buffers such as phosphate, citrate, tris or sodium acetate and other organic acids; antioxidants such as ascorbic acid; low molecular weight polypeptides (less than approximately 10 residues), proteins such as serum albumin, gelatin or immunoglobulins; hydrophilic polymers such as polyvinylpyrrolidone; amino acids such as glycine, glutamine, asparagine, arginine, leucine or lysine; monosaccharides, disaccharides and other carbohydrates, for example glucose, sucrose, mannose, lactose, citrate, trehalose, maltodextrin or dextrin; chelating agents such as EDTA; sugar alcohols such as mannitol or sorbitol; salt-forming counter-ions such as sodium, and/or non-ionic surface-active substances such as Tween, Pluronics or polyethylene glycol (PEG).

Such pharmaceutical compositions may further contain one or more diluents, fillers, binders, and other excipients, depending on the administration mode and dosage form contemplated. Examples of therapeutically inert inorganic or organic carriers known to those skilled in the art include, but are not limited to, lactose, corn starch or derivatives thereof, talc, vegetable oils, waxes, fats, polyols such as polyethylene glycol, water, saccharose, alcohols, glycerin and the like. Various preservatives, emulsifiers, dispersants, flavorants, wetting agents, antioxidants, sweeteners, colorants, stabilizers, salts, buffers and the like can also be added, as required to assist in the stabilization of the formulation or to assist in increasing bioavailability of the active ingredient(s) or to yield a formulation of acceptable flavor or odor in the case of oral dosing. The muteins of the instant invention can be administered alone, or in various combinations, and in combination with other therapeutic compositions.

The IL-4 antagonist of the invention is normally stored in lyophilized form or in solution. The IL-4 antagonists of the invention are typically water soluble and available as a dry solid to be administered as a dry powder, or reconstituted in water or saline. Respirable powders for pulmonary delivery can be produced by a variety of conventional techniques, such as jet milling, spray drying, solvent precipitation, supercritical fluid condensation, and the like.

Pulmonary delivery represents a nonparenteral mode of administration of the drug to the circulation. The lower airway epithelia are highly permeable to a wide range of proteins of molecular sizes up to about 20 kDa. Micron-sized dry powders containing the medicament in a suitable carrier such as mannitol, sucrose or lactose may be delivered to the distal alveolar surface using dry powder inhalers (DPI) such as those of Nektar™, Vectura (Gyrohaler™), and GSK (Discus™), or Astra (Turbohaler™) propellant based metered dose inhalers. Solution formulations with or without liposomes may be delivered using ultrasonic nebulizers such as those of PARI (LC Plus™) and Aerogen (Aeroneb Pro™).

The compositions of the invention can also have formulations whereby the modified human IL-4 receptor antagonists are in a delayed-released format. Suitable examples of preparations having a delayed release are, for example, semi-permeable matrices consisting of solid hydrophobic polymers which contain the protein; these matrices are shaped articles, for example film tablets or microcapsules. Examples of matrices having a delayed release are polyesters, hydrogels [e.g. poly(2-hydroxyethyl methacrylate)—described by Langer et al., *J. Biomed. Mater. Res.,* 15:167-277 [1981] and Langer, *Chem. Tech.,* 12:98-105 [1982]—or poly(vinyl alcohol)], polyactides (U.S. Pat. No. 3,773,919, EP 58,481), copolymers of L-glutamic acid and gamma-ethyl-L-glutamate (Sidman et al., *Biopolymers,* 22:547-556 [1983]), non-degradable ethylene/vinyl acetate (Langer et al., loc. sit.), degradable lactic acid/glycolic acid copolymers such as Lupron Depot™ (injectable microspheres consisting of lactic acid/glycolic acid copolymer and leuprolide acetate) and poly-D-(–)-3-hydroxybutyric acid (EP 133,988). While polymers such as ethylene/vinyl acetate and lactic acid/glycolic acid enable the molecules to be released for periods of greater than 100 days, the proteins are released over relatively short periods of time in the case of some hydrogels. If encapsulated proteins remain in the body over relatively long periods of time, they can then be denatured or aggregated by moisture at 37° C., resulting in a loss of biological activity and possible changes in immunogenicity. Meaningful strategies for stabilizing the proteins can be developed, depending on the mechanism involved. If it is found, for example, that the mechanism which leads to the aggregation is based on intermolecular S—S bridge formation as a result of thiodisulphide exchange, stabilization can be achieved by modifying the sulphydryl radicals, lyophilizing from acid solutions, controlling the moisture content, using suitable additives and developing special polymer/matrix compositions.

The formulations of the invention exhibiting delayed release also include modified human IL-4 receptor antagonists which are enclosed in liposomes. IL-4 antagonist-containing liposomes are prepared by methods which are known per se: DE 3,218,121; Epstein et al., *Proc. Natl. Acad. Sci. USA,* 82; 3688-3692 (1985); Hwang et al., *Proc. Natl. Acad. Sci. USA,* 77:4030-4034 (1980); EP 52,322; EP 36,676; EP 88,046; EP 143,949; EP 142,641; Japanese Patent Application 83-118008; U.S. Pat. Nos. 4,485,045 and 4,544,545; and also EP 102,324. As a rule, the liposomes are of the small (approximately 200-800 Angstrom) unilamellar type having a lipid content of greater than approximately 30 mol % cholesterol, with the proportion in each case being adjusted for the optimum IL-4 antagonists. Liposomes exhibiting an extended circulation time are disclosed in U.S. Pat. No. 5,013,556.

Other formulations of the invention include albumin microspheres, microemulsions, nanoparticles, nanocapsules and macroemulsions. Such techniques are mentioned in Remington's Pharmaceutical Sciences, 16th edition, Osol, A., Ed. (1980), which is incorporated herein by reference.

The following examples are intended to illustrate but not limit the invention.

Example 1

Fermentation of *E. coli*

Cells containing genes for the production of muteins were grown in LB medium (10 g Bacto tryptone, 5 g Yeast extract, 10 g NaCl per liter, pH 7.5) until OD600 reached 0.8-1.0. Expression was induced by addition of IPTG to a final concentration of 0.5 mM and incubation continued for 5 hours. Cells were harvested by centrifugation. *E. coli* transformants expressing hIL4 mutant proteins were cultured as described in U.S. Pat. No. 6,130,318. Briefly, *E. coli* were fermented in LB nutrient solution of the following composition: Bacto tryptone 10 g/l, Bacto yeast extract 5 g/l, and sodium chloride 10 g/l. The constituents were dissolved in deionized water, which was sterilized at 121° C. for 20 min. Prior to inoculation, an antibiotic which was suitable for selecting the transformants (e.g., 100 mg/l Na ampicillin or 50 mg/l kanamycin sulphate depending on the selection marker used in the vector) was added to the nutrient solution under sterile conditions. Strain stocks of all the *E. coli* transformants were laid down by taking 2 ml aliquots of a preliminary culture and storing them in liquid nitrogen. The preliminary culture fermentations were carried out in 1 ltr. shaking flasks which contained 200 ml of LB nutrient solution. The nutrient solution was inoculated with a strain stock or with a single colony from an LB agar plate. The cultures were incubated at 30° C. for 12-18 hrs. while being shaken continuously.

The main culture fermentations were carried out in LB nutrient solution using 10 liter stirred tank fermenters. The nutrient solution was inoculated with 1-5% by vol. of a preliminary culture, with the biomass being centrifuged out of the preliminary culture and resuspended in fresh LB medium prior to the inoculation. The fermentation conditions for the 10 liter main culture were as follows: 37° C., stirrer revolution rate 500 rpm, aeration rate 0.5 vvma.

In order to monitor the growth of the biomass, sterile samples were removed from the culture broth at intervals of approx. 1 hr., and their optical density was determined at 600 nm (OD600). The cultures were induced when an OD600 of 0.8-1.2 had been reached. Induction took place as follows, IPTG induction: Sterile addition of isopropyl-β-D-thio-galactopyranoside (IPTG) to a concentration of 0.4 mM. The induction time was typically 4-8 hrs.

After the fermentation had finished (6-14 hrs.), the contents of the fermenter were cooled down to 10-15° C., and the bacterial cells were harvested using standard centrifugation techniques (e.g., bucket centrifuge). The cell mass which was obtained after centrifugation was temporarily stored, where appropriate, in the frozen state. The product was worked up from the biomass which had been obtained in this way.

Example 2

Expression of Interleukin 4 Mutant Proteins in *E. coli* Using Inducible Promoters Surprisingly, a custom made vector system and a *E. coli*-codon optimized gene of the IL-4 mutein has demonstrated that bacteria transformed with said plasmid according to U.S. Pat. No. 6,506,590 gives expression rates, plasmid and expression stability values many times higher than those observed after transforming the identical hosts with plasmids known in the art.

The *E. coli* phage T5 promoter together with two lac operator sequences is derived from the pQE30 plasmid (Qiagen) belonging to the pDS family of plasmids (Bujard et al., Methods Enzymol. 155, 416-433, 1987; and Stuber et al., Immunological Methods, I. Lefkovits and B. Pernis, eds., Academic Press, Inc., Vol. IV, 121-152, 1990).

The ribosomal binding site (rbs) is derived from the region upstream from gene 10 of the phage T7 (T7 g 10 leader). Gene 10 of phage T7 codes for the coat protein, which is the major protein expressed after T7 infection. The T7 g 10 rbs was obtained from the vector pET-9a (Studier et al., Methods Enzymol. 185, 60-89, 1990). The T7 g10 leader spans a region of about 100 bp (Olins et al., Gene 227-235, 1988). In the final expression construct the region upstream of the XbaI site is deleted. The T7 g10 leader sequence now spans 42 bp and harbors one base exchange from G to A in position 3638 of the preferred plasmid.

As an effective measure of synonymous codon usage bias, the codon adaptation index (CAI) can be useful for predicting the level of expression of a given gene (Sharp et al., Nucleic Acids Res. 15, 1281-1295, 1987; and Apeler et al., Eur. J. Biochem. 247, 890-895, 1997). The CAI is calculated as the geometric mean of relative synonymous codon usage (RSCU) values corresponding to each of the codons used in a gene, divided by the maximum possible CAI for a gene of the same amino acid composition. RSCU values for each codon are calculated from very highly expressed genes of a particular organism, e.g., $E.$ $coli$, and represent the observed frequency of a codon divided by the frequency expected under the assumption of equal usage of the synonymous codons for an amino acid. Highly expressed genes, e.g., genes encoding ribosomal proteins, have generally high CAI values.gtoreq.0.46. Poorly expressed genes like lacI and trpR in $E.$ $coli$ have low CAI values.ltoreq.0.3. The calculated $E.$ $coli$ CAI value for the natural IL-4 sequence is 0.733. This means that the natural gene should be well-suited for high level expression in $E.$ $coli$. Nevertheless a synthetic gene with optimal $E.$ $coli$ codon usage (CAI value=1) has the potential to further increase the expression level. Therefore synthetic IL-4 and IL-4 mutein genes were designed and cloned.

A T7 DNA fragment containing the transcription terminator Tϕ is derived from the vector pET-9a (Studier et al., Methods Enzymol. 185, 60-89, 1990). Transcriptional terminators determine the points where the mRNA-RNA polymerase-DNA complex dissociates, thereby ending transcription. The presence of a transcriptional terminator at the end of a highly expressed gene has several advantages: they minimize sequestering of RNA polymerase that might be engaged in unnecessary transcription, they restrict the mRNA length to the minimal, thus limiting energy expense, as strong transcription may interfere with the origin of replication, a transcriptional terminator increases plasmid stability due to copy number maintenance (Balbas and Bolivar, Methods Enzymol. 185, 14-37, 1990).

The kan resistance gene is derived from the vector pET-9a (Studier et al., Methods Enzymol. 185, 60-89, 1990). Originally, this is the kan gene of Tn903 from the vector pUC4KISS (Barany, Gene 37, 111-123, 1985). In the preferred plasmid the kan gene and the IL-4 and IL-4 mutein gene have opposite orientations, so there should not be an increase in kan gene product after induction due to readthrough transcription from the T5 promoter. Kanamycin was chosen as selective marker because it is the preferred antibiotic for GMP-purposes. In addition, kan gene based vectors are more stable than ampicillin resistant (bla) plasmids. Ampicillin selection tends to be lost in cultures as the drug is degraded by the secreted β-lactamase enzyme. The mode of bacterial resistance to kanamycin relies upon an aminoglycoside phosphotransferase that inactivates the antibiotic.

Controlled gene expression is absolutely necessary for the set-up of a stable plasmid system, particularly if the protein of interest is deleterious to the host cell. The preferred plasmid uses a lac-based inducible system consisting of a lac repressor gene (lacI) and two synthetic lac operator sequences fused downstream to the $E.$ $coli$ phage T5 promoter. The lacI.sup.q promoter and the lacI structural gene were isolated from the vector pTrc99A (Amann et al., Gene 69, 301-315, 1988). I.sup.q is a promoter mutation which leads to overproduction of the lacI repressor. The wild-type lac repressor is a tetrameric molecule comprising four identical subunits of 360 amino acids each. The lac repressor tetramer is a dimer of two functional dimers. The four subunits are held together by a four-helix bundle formed from residues 340-360. Due to the isolation of the lacI gene from the vector pTrc99A by a NarI cut the residues beyond amino acid 331 are deleted and 10 amino acids not normally encoded in the lacI gene are added. It is known that mutations or deletions that occur in the C-terminal part of lacI, beyond amino acid 329, result in functional dimers that appear phenotypically similar to the wild-type repressor (Pace et al., TIBS 22, 334-339, 1997).

The origin of replication (ori) of the preferred plasmid is derived from the vector pET-9a, the ori of which originates from pBR322. The preferred plasmid therefore carries the pMB1 (ColE1) replicon. Plasmids with this replicon are multicopy plasmids that replicate in a 'relaxed' fashion. A minimum of 15-20 copies of plasmid are maintained in each bacterial cell under normal growth conditions. The actual number for the preferred plasmid is within this range. Replication of the ColE1-type ori is initiated by a 555-nucleotide RNA transcript, RNA II, which forms a persistent hybrid with its template DNA near the ori. The RNA II-DNA hybrid is then cleaved by RNase H at the ori to yield a free 3'OH that serves as a primer for DNA polymerase I. This priming of DNA synthesis is negatively regulated by RNA I, a 108-nucleotide RNA molecule complementary to the 5' end of RNA II. Interaction of the antisense RNA I with RNA II causes a conformational change in RNA II that inhibits binding of RNA II to the template DNA and consequently prevents the initiation of plasmid DNA synthesis. The binding between RNAs I and II is enhanced by a small protein of 63 amino acids (the Rop protein, Repressor of primer), which is encoded by a gene located 400 nucleotides downstream from the origin of replication (Sambrook et al., Molecular Cloning, Cold Spring Harbor, 1989). Deletion of the rop gene leads to an increase in copy number and due to a gene dosage effect to enhanced expression levels of the plasmid encoded heterologous gene. This observation was also made for the IL-4 expression vectors tested. But it turned out that rop-plasmids are instable and lost very rapidly during fermentation under non-selective conditions. Therefore, the replicon of the preferred plasmid contains the rop gene to ensure high plasmid stability. The preferred plasmid lacks the mob gene that is required for mobilization and is therefore incapable of directing its own conjugal transfer from one bacterium to another.

Example 3

Preparation of an IL-4 Mutant Protein

Cell disruption and isolation of the inclusion bodies: 25 g of $E.$ $coli$ moist mass from Example 1 were taken up in 200 ml of buffer (0.1 M phosphate buffer, pH 7.3, 0.1% Triton, 1 mM EDTA, 1 μg/ml pepstatin) and disrupted by sonication (Branson B 15 sonifier). The inclusion bodies, which contain the product, were isolated by centrifugation (35,000×g, 20 min) and washed in disruption buffer which additionally contained 4M urea.

The washed inclusion bodies were solubilized in 125 ml of buffer (0.2 M Tris, pH 8.1, 8M guanidine hydrochloride). 4 g of sodium sulphite and 2 g of potassium tetrathionate were added and the reaction mixture was stirred for 2 h. Undissolved constituents were removed by centrifugation (35,000× g, 20 min) after the reaction had finished. The supernatant was loaded onto a gel filtration column (Sephacryl S-300 HR, Pharmacia, 10×90 cm) and subjected to gel filtration in PBS buffer containing 6M guanidine hydrochloride at a flow rate of 280 ml/h. Product-containing fractions were identified by means of SDS-PAGE and combined.

β-Mercaptoethanol (final concentration 15 mM) was added in order to reduce the molecules. Following a two-hour incubation at room temperature, the mixture was diluted 5 times with water and dialyzed against buffer (3 mM $NaH_2PO_4$, 7 mM $Na_2HPO_4$, 2 mM KCl, 120 mM NaCl) for 3-4 days. The dialyzed material was adjusted to pH 5.0 with acetic acid and its conductivity was decreased to .ltoreq.10 mS/cm by adding water. 50 ml of CM Sepharose-FF (Pharmacia), which was equilibrated with 25 mM ammonium acetate, pH 5.0, were added to the mixture while stirring. Unbound material was filtered off and the gel was used to fill a column. The product was eluted with a linear gradient from 0 to 1 M NaCl in 25 mM ammonium acetate, pH 5.0, at a flow rate of 300 ml/h. Product containing fractions were identified by SDS-PAGE or by analytical RP chromatography.

The pool of CM sepharose was loaded on to a Vydac C-4 column (1×25 cm, 10 μm) which was equilibrated with 0.1% TFA and eluted with an increasing gradient of acetonitrile. Fractions which contained the pure product were combined and lyophilized.

Example 4

IL-4 Mutant Protein Decreases Pre-Existing Asthma in a Therapeutic Primate Model The therapeutic effect of IL-4RA subcutaneous treatment on allergen-induced airway inflammation and airway hyperresponsiveness (an animal model of asthma) was evaluated in Cynomolgus monkeys naturally allergic to *Ascaris suum* antigen as shown in (FIG. 1). For these experiments, the study period was extended to 24 days during which animals received inhaled antigen challenges on Days 3, 5, 7, 12, 14, 19 and 21. Airway responsiveness to inhaled methacholine and airway cellular composition (BAL) were examined on Days 0, 10, 17 and 24. The first treatment with IL-4RA (0.5 mg/kg, s.c.) occurred following assessment of airway responsiveness and airway inflammation on Day 10 and continued twice daily on each consecutive day through to Day 23 (total of 14 days treatment). Thus, this study was designed to assess the efficacy of IL-4RA in reversing existing airway inflammation and airway hyperresponsiveness.

Figure 2A:
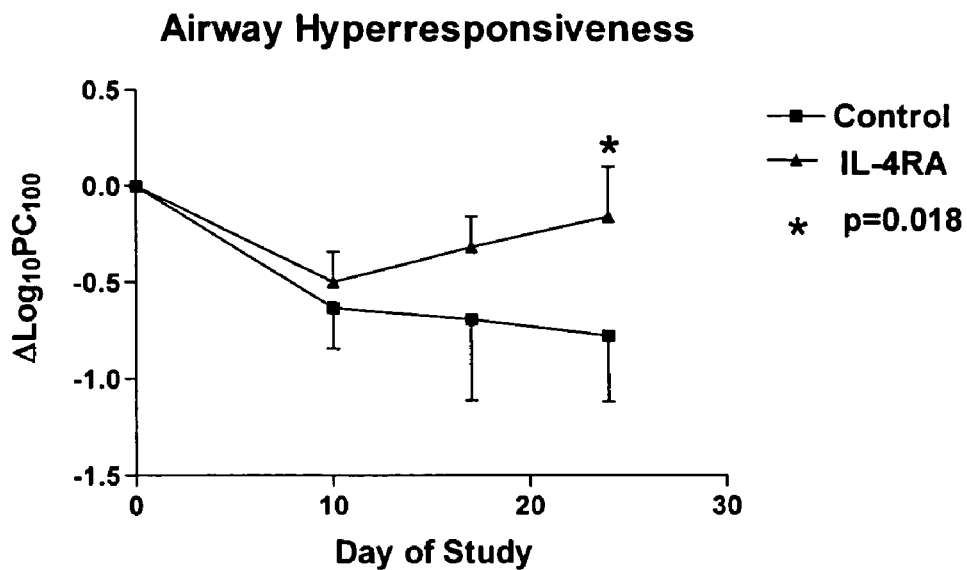
FIGS. 2A and 2B are graphical representations showing results of therapeutic intervention with subcutaneous delivery of IL-4RA on allergen-induced airway hyperresponsiveness and airway eosinophilia in non-human primates.
Figure 2B:
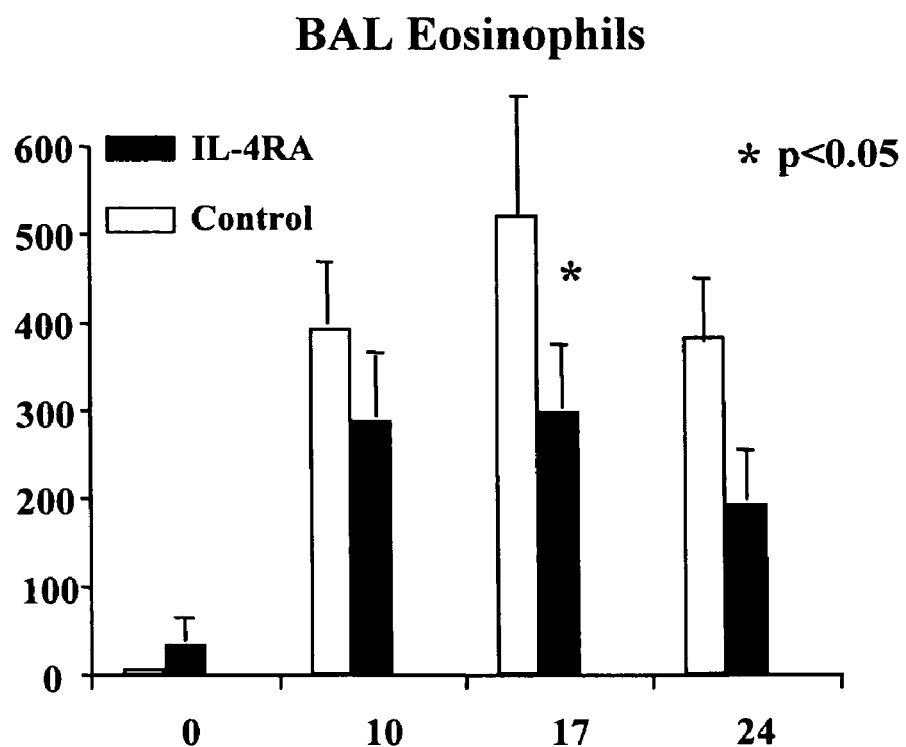

In contrast to vehicle treatment control studies, administration of IL-4RA (0.5 mg/kg/bid, s.c.) prevented any further increase in airway hyperresponsiveness at study Day 17, and reversed airway hyperresponsiveness by approximately −79% at Day 24 (p=0.018, FIG. 2a). An effect of IL-4RA treatment on airway inflammation was also observed. Net eosinophil influx was significantly reduced (p=0.05) at Day 17 and appeared still reduced on Day 24 (FIG. 2b, Values are means±SD, n=6).

These studies demonstrate that IL-4RA, administered subcutaneously, can effectively reverse airway hyper-responsiveness in the presence of continued antigen challenge suggesting that this compound may have therapeutic utility in clinical disease.

Example 5

Study of IL-4 Mutant Protein Delivered Subcutaneously to Human Asthmatics

The effect of subcutaneous (s.c.) IL-4RA on allergen-induced changes in lung function, airway hyperresponsiveness and other signs and symptoms associated with asthma was assessed in 24 asthmatics in a single center, randomized, double blind, placebo-controlled, parallel group study. Subjects were treated daily with 25 mg IL-4RA s.c. (n=12) or placebo (sterile saline, n=12) for 28 days and late asthmatic response (LAR) to allergen challenge (as measured by the forced expiratory volume in 1 sec (FEV1)) was evaluated as the primary endpoint. Additionally, the effect on inhaled methacholine airway responsiveness was evaluated. Since patients were maintained on their current therapy during the trial, medication use was monitored along with patient reporting of symptoms.

Figure 3:
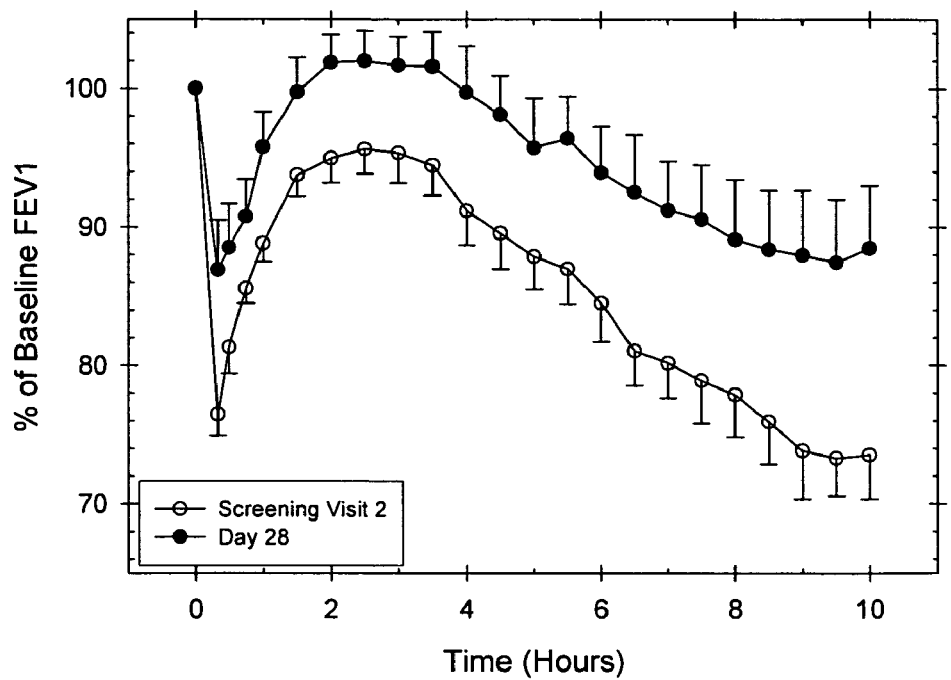
FIG. 3 is a graphical representation showing results of daily subcutaneous IL-4RA effect on antigen challenge response before treatment (Screening Visit 2) and at the end of treatment in asthmatic patients (Day 28).
Figure 4:
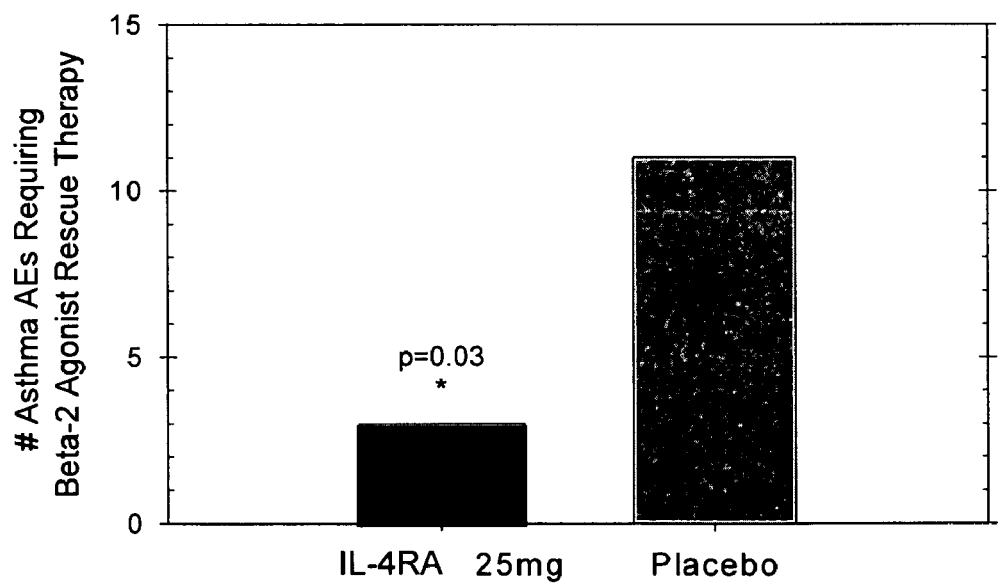
FIG. 4 is a graphical representation showing results of daily subcutaneous IL-4RA effect on adverse events (AEs) requiring β-agonists in asthmatic patients.

Relative to placebo, the IL-4RA treated group showed a 46% improvement in LAR (p=0.05) and a 26% improvement in the maximum fall in FEV1. FIG. 3 shows the improvement in the treated group from before drug (screening visit 2) to after the last treatment on Day 28. There was also a trend toward improvement in methacholine airway responsiveness in patients that received IL-4RA. In addition to positive effects on the subjects' lung function, those who received IL-4RA reported 57% fewer and milder asthma-related adverse events (6 events in 4 subjects with 3 requiring β-agonists) than subjects who received placebo (14 events in 6 subjects with 11 requiring β-agonists). The difference between placebo and IL-4RA treated patients needing β-agonist therapy was significant (p=0.03, FIG. 4).

Example 6

Figure 5:
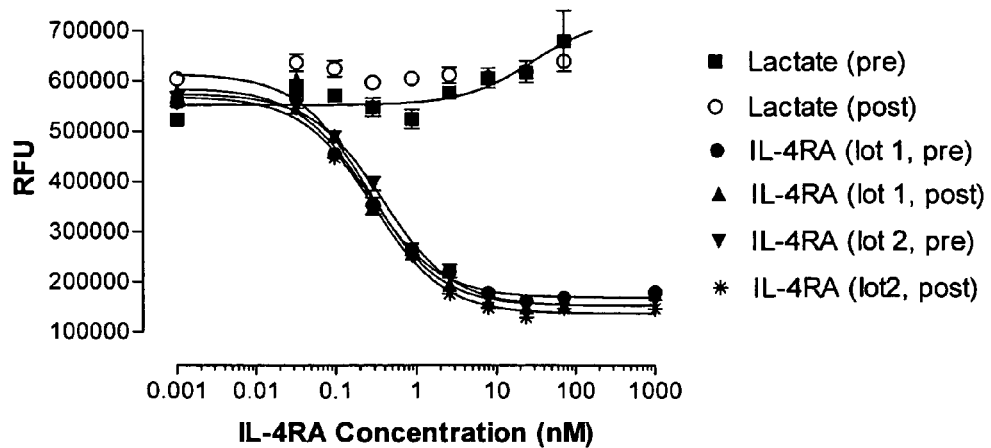
FIG. 5 is a graphical representation showing bioactivity evaluation in a TF-1/IL-4 proliferation activity assay of IL-4RA (lactate formulation) pre and post nebulization using an Aerogen Aeroneb nebulizer.

Aerosol Characterization of an IL-4 Mutant Protein in Aeroneb Pro® for Use in Non Human Primate Studies Prior to studies in non human primate the effect of aerosolization on the stability of IL-4RA has been determined. Solutions of IL-4RA (5 mL), citrate or lactate formulations ±0.01% tween, were placed in an Aerogen Aeroneb Pro™ nebulizer and the nebulizer was run to dryness. IL-4RA samples were collected pre and post nebulization and assayed for concentration, aggregation and activity. Protein concentration was assessed using several methods. No differences in protein concentration were determined via a Bradford type method or RP-HPLC in pre and post nebulized samples. SEC measurements also demonstrated 95-101% protein recovery in the post nebulized samples. Additionally, SEC-HPLC demonstrated that no soluble aggregates were present in the samples. SDS-PAGE analysis was performed to determine if nebulization of the solutions resulted in degradation of IL-4RA. No evidence of degradation products such as aggregates or fragments were observed in the top of the gel, indicative of large insoluble aggregates, or in the gel itself. Activity of IL-4RA in the pre- and post-nebulized samples was assessed in a TF-1/IL-4 proliferation assay. The ability of IL-4RA to inhibit IL-4-induced cell proliferation ($EC_{50}$ approximately 0.2-0.3 nM) was not reduced following nebulization as demonstrated by a comparison of $EC_{50}$ values determined from pre and post nebulization samples (FIG. 5). The binding activity of IL-4RA to IL-4receptor alpha chain in nebulized samples was measured using a Biacore assay. The results indicated no difference between pre- and post-nebulized samples with a Kd of approximately 0.1 nM obtained. The data demonstrate that protein content, activity and integrity of IL-4RA were maintained following nebulization.

Example 7

Inhalation Study of IL-4 Mutant Protein in Monkeys

The effect of aerosolized IL-4RA on allergen-induced airway inflammation and airway hyperresponsiveness (an animal model of asthma) was evaluated in Cynomolgus monkeys naturally allergic to *Ascaris suum* antigen. The studies were performed using a 7 day primate asthma model. Airway responsiveness to inhaled methacholine and airway cellular composition by bronchoalveolar lavage (BAL) were determined 2 days before (Day 0) and 2 days after (Day 7) three consecutive-day (Days 3, 4, 5) inhalations of *Ascaris suum* extract. Treatment studies were bracketed by control studies to assure that no changes in sensitivity to antigen occurred over time. All animals were rested 4 to 6 weeks between control and treatment studies to allow airway responsiveness and inflammation to return to baseline (pre-antigen) levels.

In this twice daily treatment study, IL-4RA was administered on the afternoon of day 2, 1 hr prior and 5 hrs after antigen challenge on days 3, 4, and 5, and in the morning and afternoon of day 6. Inhaled IL-4RA was evaluated at nominal doses in the nebulizer device of 0.5, 1.0, and 3.0 mg (in a volume of 3 ml). Inhalation studies were performed using an Aerogen Aeroneb Pro nebulizer system, coupled to a Bird Mark 7A respirator. Using this system, IL-4RA has been shown to retain activity and integrity following nebulization (Example 6). During aerosol delivery, animals were ventilated via an endotracheal tube using 5 breaths/min (20 cmH$_2$0 inspiratory pressure cut-off) with a 5 sec breath hold. The change in log methacholine provocative concentration (PC 100, mg/ml) and change in BAL total cell number and eosinophil number from Day 0 to Day 7 were determined for the two bracketing control studies and averaged for comparison to the treatment study.

Figure 6:
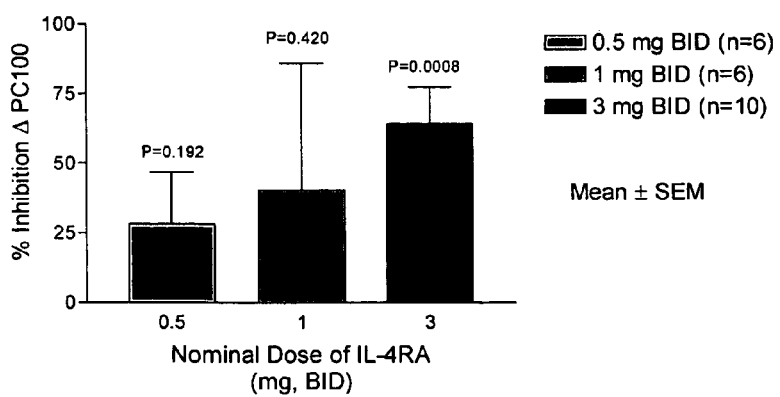
FIG. 6 is a graphical representation showing the effects of inhaled IL-4RA delivered twice daily (BID) on antigen-induced airway hyperresponsiveness in non human primates.

The effects of twice daily inhaled IL-4RA on antigen-induced airway hyperresponsiveness are shown in FIG. 6 (n=6-10, mean±SEM). Inhaled IL-4RA effectively prevented the induction of antigen-induced airway hyperresponsiveness in a dose-dependent manner, reaching a maximum inhibitory effect of 64% (p<0.001) at a nominal dose of 3 mg BID.

Figure 7:
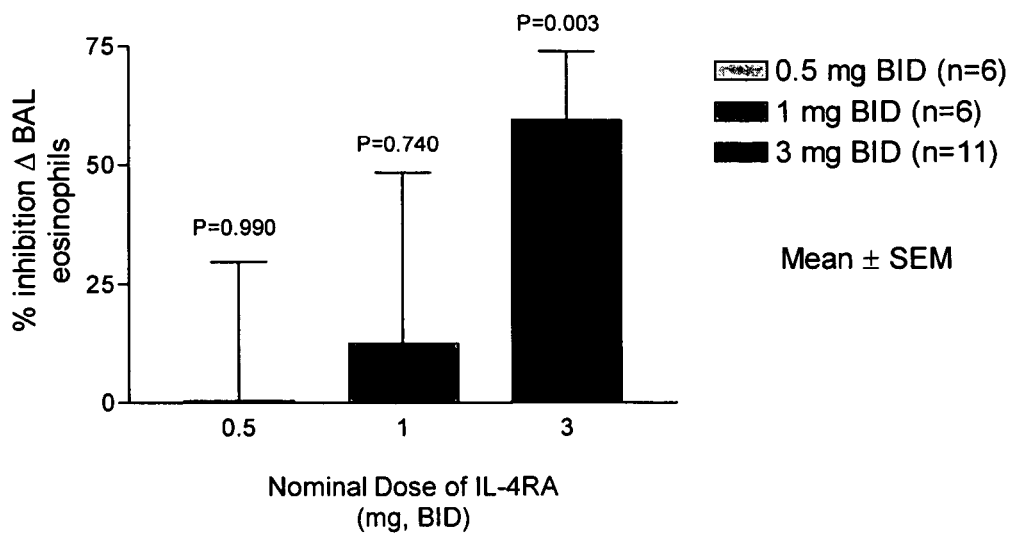
FIG. 7 is a graphical representation showing the effects of inhaled IL-4RA delivered twice daily (BID) on antigen-induced airway (BAL) eosinophilia in non human primates.

An effect of inhaled IL-4RA on airway inflammation was also observed. Inhaled IL-4RA delivered twice daily (BID) on antigen-induced airway (BAL) eosinophilia (n=6-10, mean±SEM), as a marker of airway inflammation was studied. A significant inhibitory effect of inhaled IL-4RA on allergen-induced BAL eosinophilia (60% inhibition, p=0.003) was observed at a nominal dose of 3 mg BID (FIG. 7). Bioavailability of inhaled IL-4RA is approximately 6-30%.

Example 8

Figure 8A:
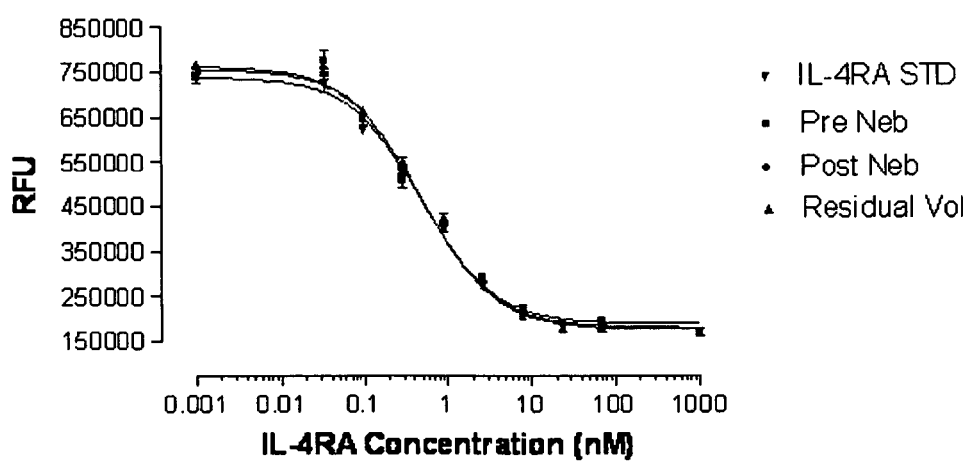
FIGS. 8A and 8B are graphical representations showing bioactivity evaluation in a TF-1/IL-4 proliferation activity assay of IL-4RA (lactate formulation) pre and post nebulization using a Pari LC Plus nebulizer.
Figures 8B, 9:
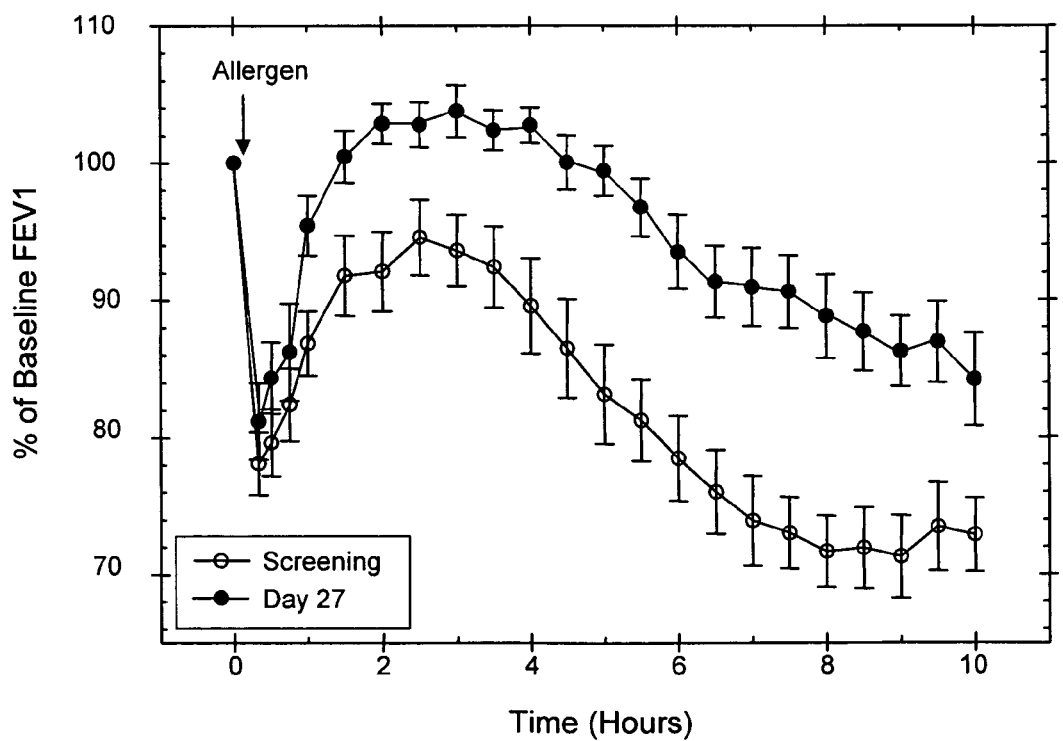
FIG. 9 is a graphical representation showing the effect of twice daily inhaled IL-4RA on antigen challenge response before treatment (Screening) and at the end of treatment (Day 27) in asthmatic patients.

Aerosol Characterization of an IL-4 Mutant Protein in Pari LC Plus® for Use in Human Asthma Studies Prior to studies in asthmatic humans, the effect of aerosolization on IL-4RA using the Pari LC Plus nebulizer and Pari Pro Neb Ultra Compressor was also determined. Solutions of IL-4RA (3 mL, lactate formulation), were placed in a Pari LC Plus™ nebulizer and the nebulizer was run to dryness. IL-4RA samples were collected pre and post nebulization and assayed for concentration, aggregation and activity. TF-1/IL-4 proliferation assay was used to evaluate activity of the post nebulized IL-4RA samples. Spectrophotometry (A280) and RP-HPLC assays were used to establish the concentration of the post nebulized sample. Integrity of IL-4RA post nebulization was confirmed by SDS-PAGE and RP-HPLC. TF-1 proliferation assay demonstrated a pre nebulization IC50 of 0.4594 nM and a post nebulization IC50 of 0.4826 nM, indicating the activity of IL-4RA was maintained following nebulization (FIGS. 8A and 8B). The integrity of IL-4RA post-nebulization was also confirmed by SDS-PAGE and RP-HPLC. In a separate study, using the same nebulizer and compressor, the mass mean aerodynamic particle size was determined using an Anderson Cascade impactor and found to be 4 µm. The fine particle fraction (% of particle below 4.7 µm and thus of respirable size) was 57%. Using a breath simulator and an adult breathing pattern, it was estimated that approximately 38% of the dose was delivered to the lung.

Example 9

Inhalation Study of IL-4 Mutant Protein in Human Asthmatics

The effect of aerosolized IL-4RA on allergen-induced changes in lung function, airway responsiveness and other signs and symptoms associated with asthma was evaluated in 30 asthmatic subjects. Equal numbers of subjects were randomized to receive either IL-4RA (60 mg) or a matched volume of placebo. Treatments were administered by nebulization from a PARI LC Plus nebulizer which has been shown to leave IL-4RA intact and fully active (Example 8). Subjects received twice daily administration of IL-4RA or placebo for 27 days and a single morning dose on Day 28. Prior to and during the study, symptoms, vital signs, ECG, exhaled nitric oxide and lung function were periodically measured. The late asthmatic response (LAR) to allergen challenge (as measured FEV1) was evaluated as the primary endpoint. Additionally, blood samples were obtained to measure IL-4RA, Anti-IL-4RA antibodies, IgE, sIL-13Rα2, IFN gamma and genetic markers of response (Single Nucleotide Polymorphisms), as well as, standard hematology and clinical chemistry parameters. On Day 27, the patients were challenged with an inhaled antigen to which they had previously demonstrated hypersensitivity, and on Day 28, airway hyperresponsiveness was examined during inhalation challenge with adenosine monophosphate (AMP).

Figure 10:
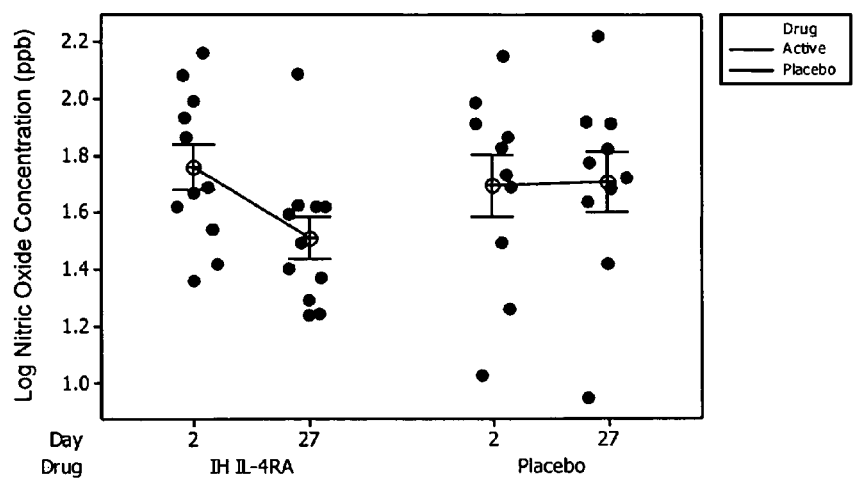
FIG. 10 is a graphical representation showing the log of nitric oxide concentration versus drug treatment on Screening Day 2 versus Day 27 in asthmatic patients.

On Day 27, compared to placebo, there was 72% reduction in the late asthmatic FEV1 response after inhalation challenge (p<0.01) to an antigen to which they had previously demonstrated hypersensitivity. FIG. 9 shows the improvement in the treated group from before drug (screening) to after the last treatment on Day 27. Similarly, there was also a reduction in airway responsiveness to AMP, compared to placebo, on Day 28. Evaluation of expired nitric oxide, a biomarker of the severity of asthma inflammation, indicated that with 27 days of treatment with twice daily inhaled IL-4RA, expired nitric oxide was decreased (FIG. 10).

Figure 11:
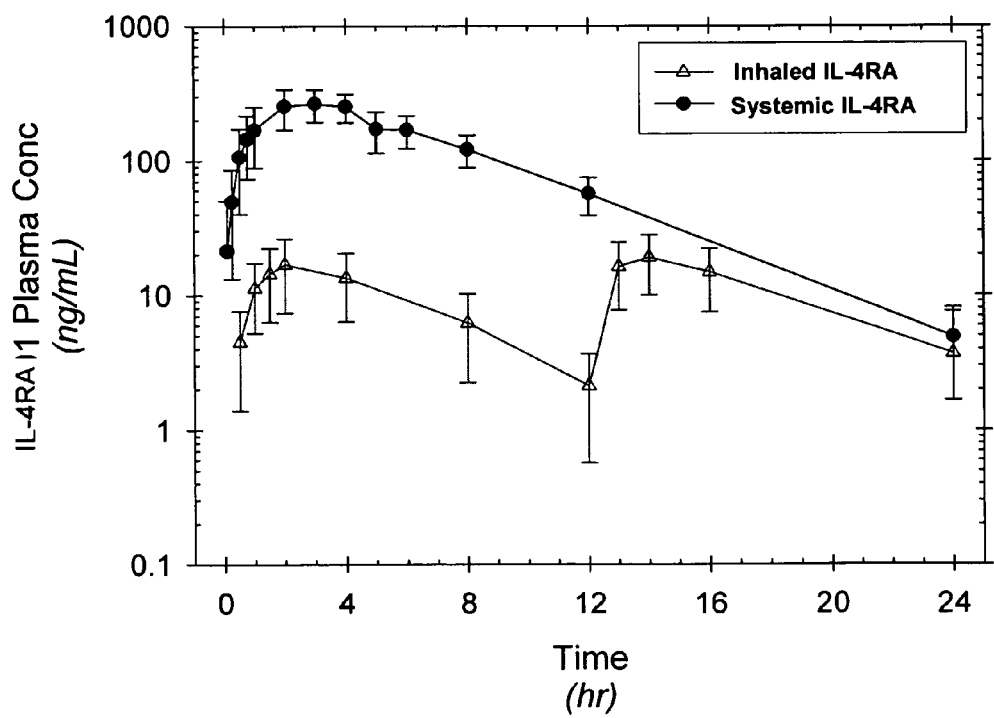
FIG. 11 is a graphical representation showing that local delivery of inhaled IL-4RA achieves plasma concentrations below the plasma concentrations achieved in the subcutaneous IL-4RA clinical trial.

IL-4RA protects subjects against the development of antigen induced decreases in lung function and decreases non specific airway responsiveness. Both monkeys and asthmatic humans show improvement in lung function after inhalation challenge to an antigen to which they have a demonstrated hypersensitivity regardless of route of exposure. The monkey data also indicate that lung inflammation, as measured by lung lavage eosinophils, is reduced with IL-4RA treatment, while reduced expired nitric oxide, symptoms and β-agonist use suggest a similar response occurs in asthmatics. Evaluation of the pharmacokinetics of IL-4RA in humans and monkeys after subcutaneous or inhalation treatment indicates that after inhalation, the systemic dose is roughly 10 times lower than the systemic exposure after subcutaneous IL-4RA treatment (FIG. 11, human; FIG. 12, monkey). This higher pulmonary, but lower systemic dose, is associated with a better or similar outcome in humans and monkeys after inhalation treatment. Taking both the monkey and the human data together, the data suggest that the effect of IL-4RA is directly on the lung and lung-associated tissue (vasculature and lymph nodes) rather than primarily mediated by other systemic organs and tissues.

Although the invention has been described with reference to the above example, it will be understood that modifications and variations are encompassed within the spirit and scope of the invention. Accordingly, the invention is limited only by the following claims.

What is claimed is:

1. A method of treating asthma comprising administering to a subject in need thereof, a pharmaceutical composition containing a therapeutically effective amount of a mutant human IL-4 (hIL-4) protein comprising the amino acid sequence of wild-type hIL-4 with two modifications, wherein the first modification is replacement of the amino acids occurring in the wild-type hIL-4 protein at positions 121 and 124 with aspartic acid, and the second modification is at least one modification selected from the group consisting of:
   a) N-terminal methionine;
   b) deletion of up to five amino acids from the C-terminus;
   c) deletion of potential glycosylation sites therein; and
   d) coupling of the protein to a non-protein polymer,
   wherein the mutant hIL-4 protein is an antagonist of wild-type hIL-4, and wherein the composition is administered for a period of at least about 28 days via inhalation, thereby ameliorating the symptoms associated with asthma.

2. The method of claim 1, wherein the second modification consists of coupling of the protein to a non-protein polymer selected from the group consisting of polyethylene glycol, polypropylene glycol, and polyoxyalkylenes, wherein the mutant hIL-4 protein is an antagonist of wild-type hIL-4.

3. The method of claim 1, wherein the composition is aerosolized prior to administration.

4. The method of claim 1, wherein the composition is nebulized as a liquid or aerosolized as a dry powder prior to administration.

5. The method of claim 1, wherein the administering occurs twice per day.

6. The method of claim 1, wherein the amount of IL-4 is about 0.3 mg.

7. The method of claim 1, wherein the amount of IL-4 is about 3.0 mg.

8. The method of claim 1, wherein the amount of IL-4 is about 30 mg.

9. The method of claim 1, wherein the amount of IL-4 is about 60 mg.

10. The method of claim 1, wherein the composition further contains a pharmaceutically acceptable carrier.

11. The method of claim 10, wherein the carrier is selected from the group consisting of lactate, citrate and sucrose buffer.

12. The method of claim 1, wherein the amount of IL-4 is about 0.1 to 1 mg/kg.

13. A method of treating asthma comprising administering to a subject in need thereof, a pharmaceutical composition containing a therapeutically effective amount of a mutant human IL-4 (hIL-4) protein comprising the amino acid sequence of wild-type hIL-4 with two modifications, wherein the first modification is replacement of the amino acids occurring in the wild-type hIL-4 protein at positions 121 and 124 with aspartic acid, and the second modification is at least one modification selected from the group consisting of:

a) N-terminal methionine;

b) deletion of up to five amino acids from the C-terminus;

c) deletion of potential glycosylation sites therein; and d) coupling of the protein to a non-protein polymer, wherein the mutant hIL-4 protein is an antagonist of wild-type hIL-4, and wherein the composition is administered for a period of at least about 28 days via subcutaneous injection, thereby ameliorating the symptoms associated with asthma.

14. The method of claim 13, wherein the second modification consists of coupling of the protein to a non-protein polymer selected from the group consisting of polyethylene glycol, polypropylene glycol, and polyoxyalkylenes, wherein the mutant hIL-4 protein is an antagonist of wild-type hIL-4.

15. The method of claim 13, wherein the amount of IL-4 is about 0.7 mg.

16. The method of claim 13, wherein the amount of IL-4 is about 7.0 mg.

17. The method of claim 13, wherein the amount of IL-4 is about 20 mg.

18. The method of claim 13, wherein the amount of IL-4 is about 30 mg.

19. The method of claim 13, wherein the amount of IL-4 is about 0.1 to 1 mg/kg.

20. The method of claim 13, wherein the administering occurs twice per day.

21. The method of claim 13, wherein the composition further contains a pharmaceutically acceptable carrier.

22. The method of claim 21, wherein the carrier is selected from the group consisting of lactate, citrate and sucrose buffer.

23. The method of claim 1, wherein the administering occurs once per day.

24. The method of claim 13, wherein the administering occurs once per day.

* * * * *